Figure 1:
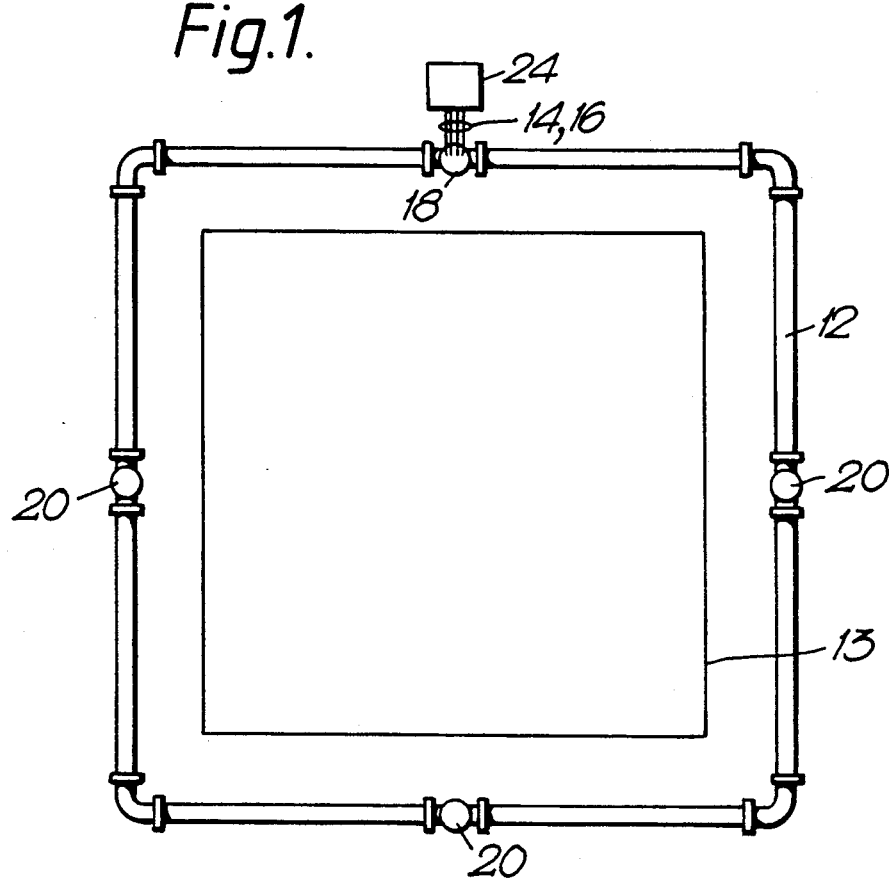

United States Patent [19]

Clarke

[11] Patent Number: 5,007,996

[45] Date of Patent: Apr. 16, 1991

[54] DETECTION SYSTEM

[75] Inventor: John R. P. Clarke, Cheadle, England

[73] Assignee: Imperial Chemical Industries PLC, London, England

[21] Appl. No.: 422,120

[22] Filed: Oct. 16, 1989

[30] Foreign Application Priority Data

Oct. 24, 1988 [GB] United Kingdom ............... 8824895
Oct. 24, 1988 [GB] United Kingdom ............... 8824896

[51] Int. Cl.$^5$ ................ G01N 27/403; G01N 27/404
[52] U.S. Cl. .................... 204/409; 204/153.1; 204/153.13; 204/153.17; 204/414; 204/415; 204/431
[58] Field of Search ............ 204/1 T, 1 P, 409, 415, 204/414, 431, 432, 153.1, 153.13, 153.17

[56] References Cited

U.S. PATENT DOCUMENTS

| 2,805,191 | 9/1957 | Hersch | 204/431 |
| 3,028,317 | 4/1962 | Wilson et al. | 204/431 |
| 3,223,608 | 12/1965 | Hersch | 204/409 |
| 3,258,415 | 6/1966 | Kordesch | 204/414 |
| 3,461,055 | 8/1969 | Staunton | 204/435 |
| 3,493,484 | 2/1970 | Berg et al. | 204/431 |
| 3,526,577 | 9/1970 | Molloy | 204/415 |
| 3,833,495 | 9/1974 | Grubb | 204/414 |
| 3,988,233 | 10/1976 | Gamer et al. | 204/409 |
| 4,207,162 | 6/1980 | Lotze | 204/414 |
| 4,626,330 | 12/1986 | Farmer | 204/197 |

Primary Examiner—T. Tung
Attorney, Agent, or Firm—Cushman, Darby & Cushman

[57] ABSTRACT

A detection system for the detection of e.g. chlorine in a gas stream comprises an elongate support (14) which has electrolyte distributed along its length and is provided with a pair of electrodes (18,20), the electrolyte being chemically reactive with the gas to be detected to produce an electric current detectable by the electrodes. The electrolyte may be distributed along the support by capillary action or it may incorporate a viscosity-enchancing agent to allow the electrolyte to remain in place along the length of the support thereby avoiding loss of electrolyte by dripping.

25 Claims, 4 Drawing Sheets

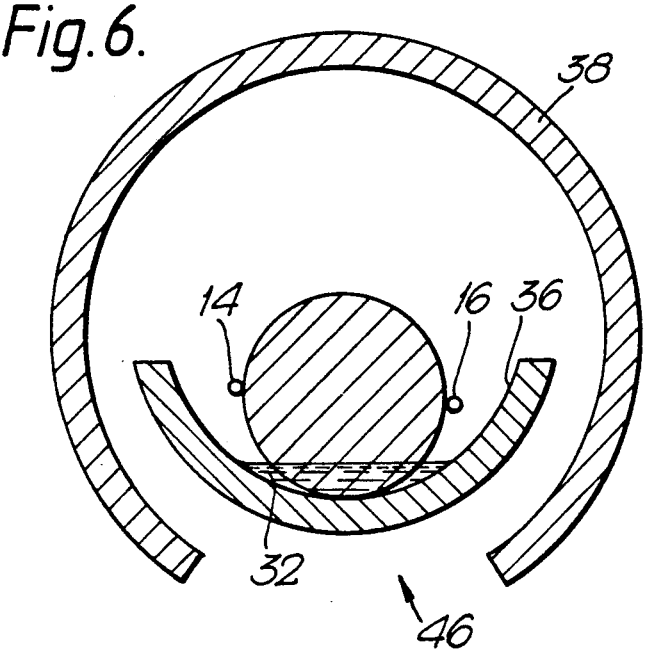
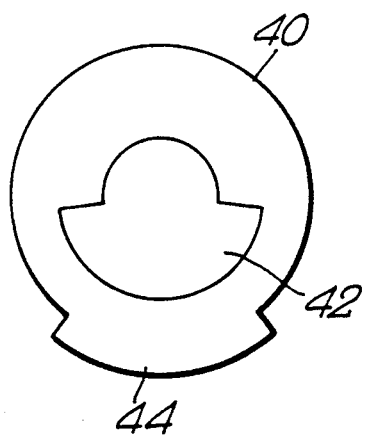
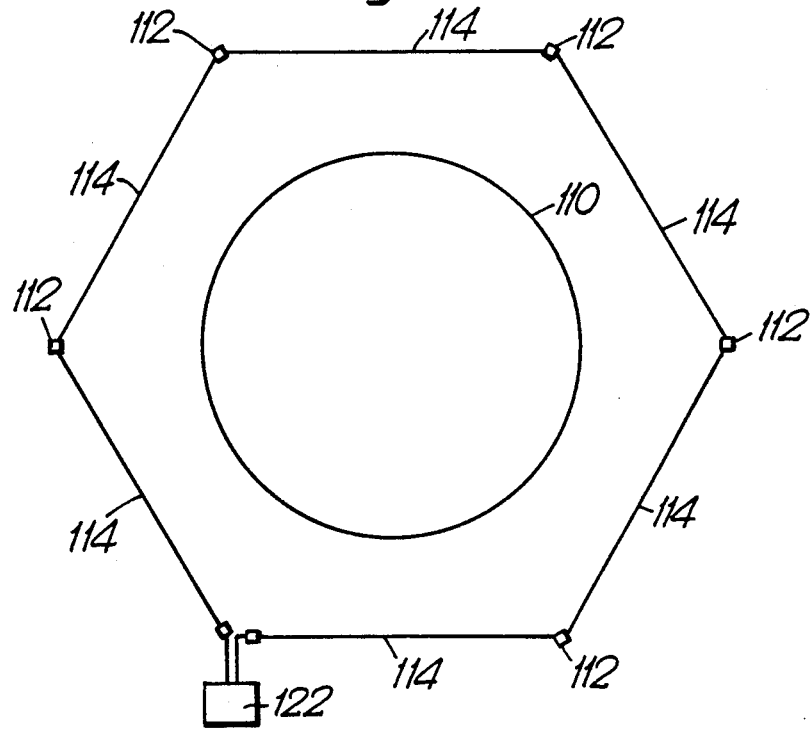

DETECTION SYSTEM

This invention relates to an electrochemical system for the detection of a fluid component, e.g. the detection of chlorine gas in a gas stream or the environment.

It is a frequent requirement in industry to detect quickly and, in many cases, monitor accurately the presence and concentration of a component of fluids, especially gases. For example there is a need for rapid detection of toxic substances such as chlorine, bromine, certain oxides of nitrogen, chlorine dioxide and ozone gas in breathable atmospheres or in process gas streams. Numerous devices have been proposed for this purpose, including electrochemical devices wherein the substance to be detected or monitored is cased to react chemically with a reagent in contact with electrodes across which is applied a low voltage potential. An electric current is generated between the electrodes as a result of the change in composition of the reagent caused by the chemical reaction. It is with this type of electrochemical device that the present invention is concerned.

A known device is disclosed in our prior British Patent No. 1552620. A drawback with known devices is that they are effectively "point" sensors in that they are capable only of detecting gas such as chlorine if present or released in closed proximity to the device and the wind or gas flow is directed towards the sensor. To some extent, this drawback could be overcome by using a large array of sensing devices in sufficiently close proximity to one another as to minimise the risk of a gas release going undetected. For example, a vessel containing a toxic gas could be encircled by a vast array of point sensor devices so as to detect any gas release occurring as a result of the vessel being breached. However, the feasibility of such an arrangement would be questionable in terms of capital cost and complexity.

According to one aspect of the present invention there is provided an electrochemical system for the detection of a fluid component, comprising two or more electrodes in contact with an electrolyte which combines with the fluid component to be detected to cause a change in an electrical parameter detectable by means of the electrodes, characterised in that the electrolyte is distributed by capillary action along an elongated element which is arranged so as to extend predominantly horizontally.

According to a second aspect of the invention there is provided an electrochemical system for the detection of a fluid component comprising two or more electrodes in contact with an electrolyte which combines with the fluid component to be detected to cause a change in an electrical parameter detectable by means of the electrodes characterised in that the electrolyte is distributed along an elongated element which contacts the contents of a reservoir of said electrolyte, means is provided for supporting the elongated element with its longitudinal axis generally horizontal, and the elongated element is arranged either alone or in combination with at least one of the electrodes to distribute the electrolyte lengthwise thereof by capillary action.

Preferably means is provided for maintaining electrolyte tending to drain away from the elongated element along its active length in contact therewith; such means may for example comprise a channel or trough in which the elongated element is received. The assembly of the elongated element and the electrodes may extend along and be supported by the base of the channel or trough. Any excess electrolyte tending to drain from or drip from the elongated element and electrode assembly simply collects at the base of the channel or trough and is therefore available for capillary feed back to the elongated element and electrode assembly.

The term "active length" is used herein to refer to that part of the elongated element which carries the electrolyte, is exposed for reaction of the electrolyte with the fluid component to be detected and is provided with the electrodes.

The channel in which the elongated element is received may be open at one side or it may have a closed periphery, i.e. a tubular configuration. In the latter event, the channel is composed of a material which is permeable to gas flow but retains liquid if the liquid is not subject to any significant pressure tending to force it through the wall or walls of the channel.

In a preferred embodiment of the invention, the elongated element has a structure per se or is composed of a material providing a wicking action and is arranged to dip into the electrolyte-containing reservoir. If desired, the system may include two or more electrolyte-containing reservoirs and the elongate element may contact the reservoirs at spaced positions along its length.

Where the elongated element functions as a wick, it preferably comprises strands or fibres woven together to form a cord, cable or string-like structure.

In general, the elongated element will be of a substantial longitudinal extent, preferably at least one order of magnitude, and more preferably at least 50 times, greater than its diameter (or major cross-sectional dimension).

The electrodes may extend generally parallel with the elongated element or one or more of the electrodes may be wound around the elongated element conveniently in helical fashion in which event the pitch of the coil is preferably substantially larger than the major cross-sectional dimension of the elongated element.

Where the elongated element is woven from strands or fibres one or more of the electrodes may be interwoven with the strands or fibres or otherwise incorporated in the body of the elongated element so that the electrodes contact the electrolyte distributed along the elongated element.

In an alternative embodiment, the capillary action may be provided by gaps present in the vicinity of the positions of contact between the electrodes and the outer periphery of the elongated element. Such gaps will exist for example when the electrodes are of round section and the elongated element is of round section. In this embodiment, the electrodes are arranged to extend in generally helical fashion around the elongated element so that, at intervals along the length of the elongated element, they (and hence the gaps along which capillary flow occurs) are immersed in the electrolyte occupying the channel or trough.

The electrolyte may be chemically reactive with said fluid component and preferably comprises an aqueous solution of a hygroscopic substance or substances or, more preferably, a deliquescent substance or substances as disclosed in our prior U.S. Pat. No. 1552620. Alternatively, the electrolyte may incorporate a humectant. The elongated element may be arranged so that it has a generally linear or curvilinear configuration and serves as a "line" sensor or it may be configured in a two dimensional or even three dimensional arrangement by, for example, mounting it in a zig-zag, meandering or like configuration in one or more planes.

The elongated element may be arranged to extend as a loop around the perimeter of a zone which is to be monitored. For example, the elongated member may have both ends immersed in a common reservoir containing the electrolyte and the remainder of the elongated member together with the electrodes may extend for instance around the periphery of a vessel containing a toxic gas so that, in the event of a breach in the integrity of the vessel at any point around its periphery or a valve or flange associated with the vessel, any gas released is detected by the sensor.

According to a further aspect of the present invention there is provided a system for the detection of a fluid component comprising two or more electrodes in contact with an electrolyte which combines with the fluid component to be detected to cause a change in an electrical parameter detectable via the electrodes, characterised in that the electrolyte is distributed along an elongated element and incorporates a viscosity-enhancing agent which renders the electrolyte substantially immobile.

The viscosity-enhancing agent may take any suitable form which is chemically compatible with the electrolyte and imparts sufficient viscosity thereto to render it substantially immobile particularly in terms of resisting flow induced by gravity and more particularly in terms of resisting loss of electrolyte by dripping of the electrolyte from non-vertical runs of the elongated element. The viscosity-enhancing agent may for example comprise a gelling agent such as a hydrogel or agar.

The elongated element preferably has an open pore structure and conveniently comprises strands or fibres woven together so that the elongated element has a cord, cable or string-like structure. In an alternative embodiment, the arrangement may be such that gaps between the electrodes and the elongated element act as reservoirs holding the electrolyte, in which case the element may comprise a rod, tube or the like.

The electrolyte may be coated on to the external surface of the elongated element or the latter may be impregnated with the electrolyte.

In one embodiment of the invention, the elongated element is ranged so as to extend predominantly horizontally and support means are provided for supporting it at spaced intervals along its length. The support means may for example comprise vertically disposed posts to which the elongated element is attachable by means of suitable connectors.

Figure 3:
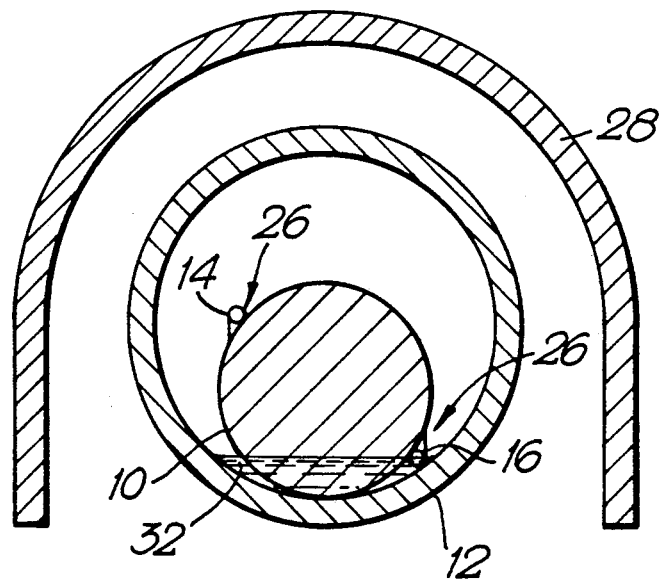
Figure 2:
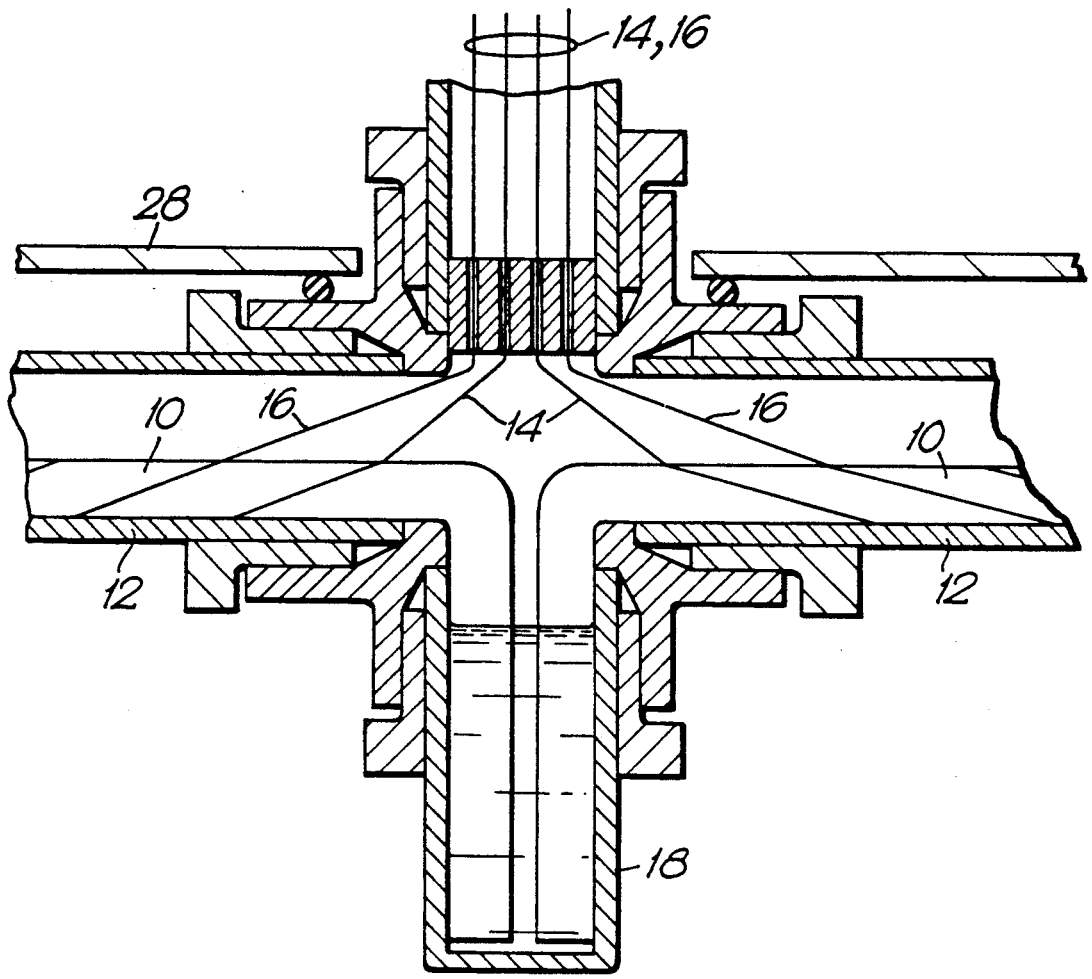
Figure 4:
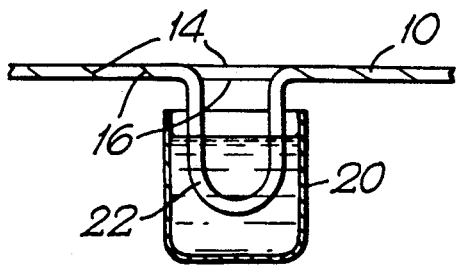
Figure 5:
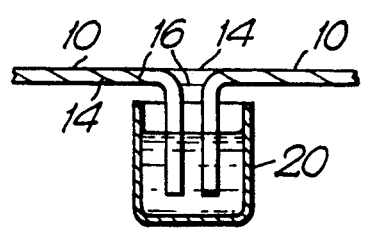
Figure 9:
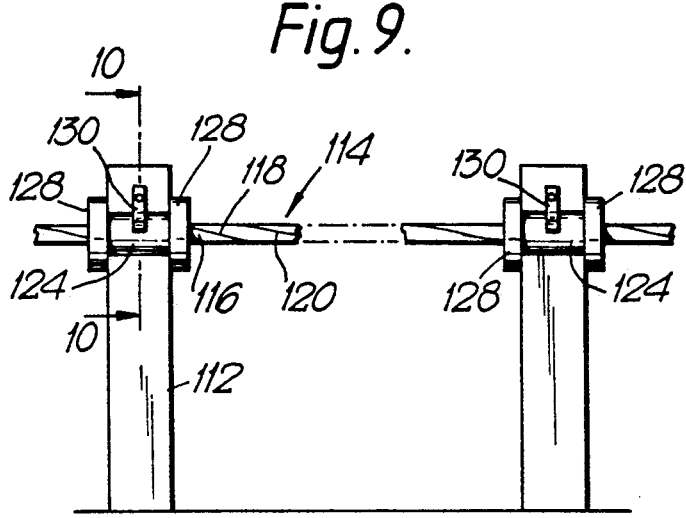
Figure 10:
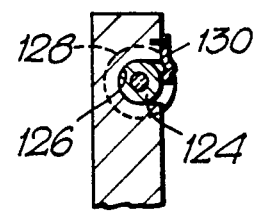
Figure 11:
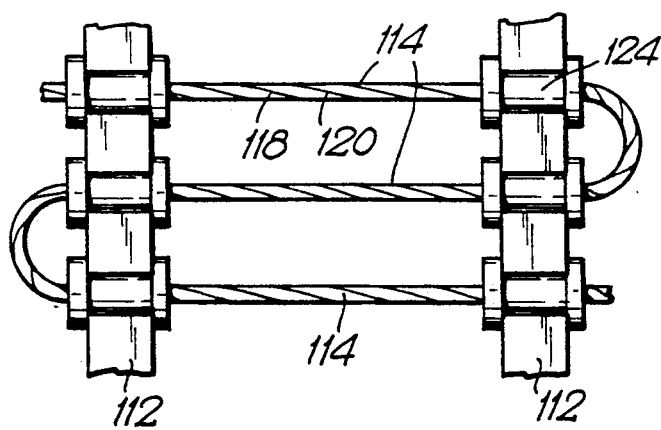
Figure 12:
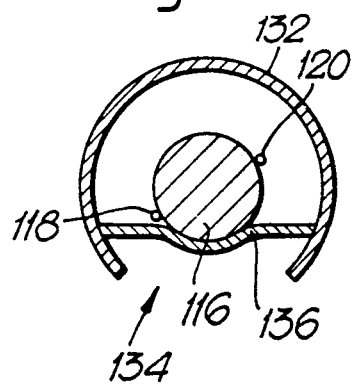

The invention will now be described by way of example only with reference to the accompanying drawings in which: FIG. 1 is a diagrammatic plan view of a system in accordance with the invention, the cover 28 being omitted; FIG. 2 is a sectioned side view of part of the system; FIG. 3 is a cross-sectional view of the system; FIG. 4 is a diagrammatic view showing one reservoir-wick arrangement; FIG. 5 is a diagrammatic view showing an alternative reservoir-wick arrangement; FIG. 6 is a view similar to FIG. 3 of a modified embodiment; FIG. 7 is an elevational view of a mounting disc for use in the embodiment of FIG. 6. FIG. 8 is a diagrammatic plan view showing a detector system according to the invention installed in boundary fence fashion around a vessel containing a toxic gas or the like; FIG. 9 is a side view showing part of the boundary fence; FIG. 10 is a view in the direction 10—10 in FIG. 9; FIG. 11 is a view similar to FIG. 9 showing the line sensor arranged in a two-dimensional configuration; and FIG. 12 is a cross-sectional view of a modified embodiment.

Referring to FIGS. 1-3, in one embodiment the detecting system of the invention comprises an elongated element 10 which extends along a generally horizontally disposed tube 12 and is arranged in the vicinity of a zone 13 which is to be monitored for the release of a gas such as chlorine. The zone 13 may for example accommodate a storage vessel containing the gas and the elongated element may be located adjacent the vessel, for instance in close proximity to a part of the vessel, such as a valve or flange, from which gas could leak in the event of a breech in the integrity of the vessel. The element 10 has an electrolyte in liquid form distributed along its length and is provided with a pair of electrode wires 14, 16 (of for example platinum or platinised niobium or platinised titanium) extending in spaced relation to one another and generally co-extensive with the element 10.

The tube 12 is adapted to allow ingress of air into its interior so that the element 10 is exposed to an air flow which, in the event of a breach in the vessel integrity, will contain the gas to be detected. Such ingress of gas may be implemented in a number of ways; for example, the tube may be slotted or provided with perforations in its wall or it may be composed at least in part of a material having inherent porosity such that the tube wall is permeable to gas but only permits egress of liquid if the latter is under significant pressure. Porous plastics materials such as porous polyfluoroethylene or porous polyethylene are commercially available and the tube may be composed, at least in part, of such material.

The electrolyte is selected according to the gas to be detected and, as previously mentioned, typically comprises an aqueous solution of a deliquescent salt. Distribution of the electrolyte along the element 10 is effected by capillary action. The necessary capillary action is, in preferred embodiments of the invention, provided by fabricating the element 10 in the form of a wick, e.g. it may comprise a cable, cord or string produced from fibres or strands. At least one end (both in the illustrated embodiment of FIG. 1) of the wicking element 10 dips into a reservoir 18 containing the electrolyte. Although the element 10 is disposed horizontally, the tendency for the aqueous electrolyte to drip is not a problem because the wicking element 10 runs along the lowermost section or base of the tube 12 (see FIG. 3) and any excess electrolyte 32 (see FIG. 3) can therefore collect at the base region of the tube 12 and is available for re-absorption into the element 10 by capillary action. If desired, as shown in FIG. 4, the element 10 may contact intermediate reservoirs 20 of electrolyte at strategic positions along its length. The element 10 may be continuous over the whole of its length in which case contact with the electrolyte in the intermediate reservoirs 20 can be effected by introducing a looped portion 22 in the element 10 (as shown diagrammatically in FIG. 4) and immersing the looped portion(s) in the reservoir(s) 20. Alternatively, as shown (diagrammatically) in FIG. 5, the element 10 may comprise separate sections extending between successive reservoirs 18, 20.

The electrode wires 14, 16 are coupled to an instrumentation console 24 and are preferably wound around the element 10 in a multi-start fashion with a slow spiral and without contacting each other. Alternatively, instead of being wound around the element, at least one of the electrode wires 14, 16 may be incorporated into the body of the element; for instance by interweaving the wire(s) 14/16 with the strands or fibres from which the element 10 is woven. The console 24 serves to impress a low voltage (i.e. below the decomposition potential of water) across the electrodes 14,16 and a change in the composition of the electrolyte resulting from localised reaction thereof with the fluid component to be detected (if present) causes a measurable electric current to flow between the electrode wires which is sensed by the instrumentation 24. The latter, in response to sensing of such a current, may for example cause actuation of visible and/or audible alarms either if any of the fluid component is detected or if the fluid component detected reaches or exceeds a predetermined level of concentration, and/or the instrumentation 24 may record and/or display the presence of the fluid component or changes in its concentration level over a period of time.

Although it is preferred to employ an element 10 which, per se, has wicking characteristics, in an alternative embodiment distribution of the electrolyte along the element 10 by capillary action may be produced by virtue of the small generally helically extending gaps 26 immediately adjacent the zones of substantially line contact between the electrode wires 14,16 and the peripheral surface of the element 10. In this case, the element 10 may have a smooth surface and may be of solid or tubular section. The wires 14,16 by virtue of their helical configuration repeatedly pass across the base region of the tube 12 thus allowing electrolyte present in the base region to be collected and fed by capillary action around and along the length of the element 10.

A cover 28 (see FIG. 3) may be provided to provide protection against the weather, particularly rain. The lengths of tube 12 may comprise commercially-available tubing and commercially-available couplings and fittings such as are used in plastic plumbing systems may be employed to produce joints and junctions between the tube lengths.

In a modified embodiment as shown in FIG. 6, instead of using a channel in the form of a tube 12 having a closed periphery, the channel along which the element 10 runs is in the form of a trough 36 mounted within a cover 38 by suitable means such as discs 40 (see FIG. 7) having a central aperture 42 through which the assembly of the trough 36 and element 10 extend and a radial projection 44 for reception in the opening 46 (which may be of a continuous or discontinuous nature lengthwise of the cover) at the underside of the cover 38. The opening(s) 46 serves as an inlet for air/gas flow into the cover for interaction with the element 10.

Referring to FIGS. 8-10, a system is shown for detection of release of a gas, such as chlorine or other toxic gas, into the surrounding atmosphere in the event of a breach in the integrity of a vessel 110 containing the gas. The system comprises a fence-like arrangement erected around the perimeter of the vessel and comprises a series of support posts 112 which support a continuous line sensor 114 extending generally horizontally from one post to the next to form a loop encircling the vessel 110. The line sensor 114 comprises a cord or string 116 woven from fibres or strands of an electrically insulating material, e.g. a plastics material and is impregnated over substantially its entire length with an electrolyte rendered substantially immobile (and hence drip-proof) by a viscosity-enhancing agent such as a hydrogel. The cord or string is provided with electrode wires 118,120 of for example platinum (or platinised titanium or platinised niobium which are substantially co-extensive with the cord 116 and extend from an instrumentation console 122 around the loop and back to the console 122. The wires 118,120 are wound around the cord 116 in a multi-start fashion with a slow spiral and without contacting each other. Alternatively, instead of being wound around the cable 116, at least one wire may be interwoven with the strands or fibres from which the cable is woven or otherwise incorporated into the body of the cable and in such a way that the wires are non-contacting.

The electrolyte may be selected so as to be chemically reactive with the fluid component to be detected—for example where chlorine is to be detected the electrolyte may comprise an aqueous solution of a deliquescent salt such as calcium bromide or the salt may be combined with a humectant such as glycerol to keep an otherwise dry salt damp. The electrolyte will additionally incorporate a viscosity-enhancing agent which will be selected so as to be chemically compatible with the electro-chemically active constituent of the electrolyte without adversely affecting to any significant extent the electrochemical interaction of the electrolyte with the fluid component to be detected. It is desirable that the active constituent of the electrolyte should be deliquescent or hygroscopic or be combined with a humectant so as to reduce susceptibility to rapid drying out as a result of evaporation of the solvent in the course of exposure to gas streams. The viscosity-enhancing agent may also be a humectant for the purpose of maintaining the salt damp.

Although specific reference is made above to the detection of chlorine, the system may be used for a wide variety of fluid components including chlorine dioxide, ozone, oxides of nitrogen; lithium-bromide for example is suitable for the detection of $NO_x$.

In use, a low voltage potential (below the decomposition potential of water) is impressed across the electrodes by means of the instrumentation 122 and a change in the composition of the electrolyte resulting from localised reaction thereof with the fluid component to be detected (if present) causes a measurable electric current to flow between the electrodes which can be sensed by the instrumentation 122. The latter, in response to sensing of such a current, may for example cause actuation of visible and/or audible alarms either if any of the fluid component in question is detected or if the fluid component detected reaches or exceeds a predetermined level of concentration, and/or the instrumentation may record and/or display the presence of the fluid component or changes in the concentration level of the fluid component over a period of time.

Referring to FIGS. 9 and 10, the particular mounting arrangement employed in this embodiment takes the form of bobbins 124 having a central bore through which the line sensor 114 passes, the bobbins 124 being designed for reception in openings 126 in the support posts 112. The bobbins 124 are restrained against axial movement relative to the support posts by flanges 128 and the bobbins 124 are releasably retained in the openings 126 by resiliently-deflectable fingers 130.

In the embodiment of FIGS. 8 to 10, the system essentially acts as a line sensor, i.e. in one dimension. As shown in FIG. 11, by appropriately configuring and supporting the cable and electrode assembly, the system may provide sensing in two dimensions and it will be seen that the system may readily take the form of a two-dimensional fence-like arrangement which may be arranged to encircle a zone to be monitored for possible release of the fluid component to be detected. In FIG. 11, the cable and electrode assembly is shown with a two dimensional configuration in the vertical plane; however it will be appreciated that a three dimensional configuration is also possible.

Although in FIGS. 8-10, the line sensor is described as being continuous, the loop may, if desired, comprise a number of separate line sensors constituting respective sections of the loop.

As shown in FIG. 12, where the line sensor is used in situations where it may be subject to the elements, especially rain, the exposed lengths of electrolyte-bearing cable 116 may be protected by means of a shield or cover 132 which can for example be supported by the bobbin flanges 128 in spaced relation with the cable 116. The cover 132 has an opening or openings 134 at its underside to permit circulation of air or the gas stream around the cable/electrode assembly. The cover 132 can be made of a rigid non-corrodable material such as a suitable plastics material and may be provided with spaced support arms 136 along its length to afford additional support for the cable/electrode assembly to prevent the latter from sagging over the span between successive posts 112. The cover 132 may if desired be made of a gas permeable material, such as a porous polyethylene, which though porous will not allow ingress of water if not under pressure—in this event, the porosity of the material may be adequate to allow ingress of gas without the need for openings such as 134 in the cover, i.e. the cover may be tubular with an uninterrupted peripheral wall.

I claim:

1. An electrochemical system for detection of a fluid component, comprising:
    at least two electrodes;
    an elongated element adapted to hold an electrolyte which combines with the fluid component to be detected to cause a change in an electrical parameter detectable by means of the electrodes, and disposed so that the electrodes are in contact with the electrolyte, the electrolyte being distributed along the length of the elongated element, which extends at least partly around a periphery of a zone containing a source from which said fluid component may be emitted or discharged;
    means for maintaining electrolyte distributed over said elongated element; and
    means for routing said element in a loop extending around the periphery of said zone such that the element is exposed to fluid flow directed outwardly from said zone and laterally towards the element at different points along its length.

2. A system as claimed in claim 1 in which said means for maintaining electrolyte distributed over said element includes a reservoir of said electrolyte which is contacted by the elongated element, said routing means including means for supporting the elongated element with its longitudinal axis generally horizontal, and the elongated element being arranged to distribute the electrolyte lengthwise thereof by capillary action.

3. A system as claimed in claim 2 in which said means for maintaining electrolyte distributed over said element is arranged to maintain electrolyte tending to drain away from the elongated element along its active length in contact therewith.

4. A system as claimed in claim 3 in which said means for maintaining electrolyte distributed over said element comprises a channel in which the elongated element is disposed.

5. A system as claimed in claim 2 in which the capillary action is effected by gaps present in the vicinity of the positions of contact between the electrodes and the outer periphery of the elongated element.

6. A system as claimed in claim 1 in which the elongated element is formed of a means for providing a wicking action and is arranged to dip into an electrolyte-containing reservoir.

7. A system as claimed in claim 6 in which the system includes at least two electrolyte-containing reservoirs and the elongated element contacts the reservoirs at spaced positions along its length.

8. A system as claimed in claim 1 in which the electrolyte incorporates a viscosity-enhancing agent which renders the electrolyte substantially immobile.

9. A system as claimed in claim 1 in which the elongated element comprises strands or fibres woven together to form a cord, cable or string-shaped structure.

10. A system for the detection of a fluid component, comprising:
    at least two electrodes;
    an elongated element, adapted to hold an electrolyte which combines with the fluid component to be detected to cause a change in an electrical parameter detectable via the electrodes, and disposed so that the electrodes are in contact with the electrolyte, the electrolyte being distributed along the elongated element and incorporating a viscosity-enhancing agent which renders the electrolyte substantially immobile; and
    means for supporting and routing said elongated element along a predetermined path which extends in a loop around the perimeter of a zone which is to be monitored for release of said fluid component such that the elongated element is exposed to fluid flow directed laterally towards the element at different points along its length.

11. A system as claimed in claim 10 in which the viscosity-enhancing agent comprises a gelling agent.

12. A system as claimed in claim 10 in which the elongated element has an open pore structure.

13. A system as claimed in claim 10 in which the arrangement is such that gaps between the electrodes and the elongated element act as reservoirs holding the electrolyte.

14. A system as claimed in claim 10 in which the electrolyte is coated onto the external surface of the elongated element.

15. A system as in claim 10 wherein the elongated element is impregnated with the electrolyte.

16. A system as claimed in claim 10 in which said routing and supporting means is arranged to support the elongated element predominantly horizontally at spaced intervals along its length.

17. A system as claimed in either of claims 15 or 16 in which the routing means comprises vertically disposed posts to which the elongated element is attachable by means of suitable connectors.

18. A system as claimed in claim 1 or claim 10 in which the length of the elongated element is at least 50 times greater than its major cross-sectional dimension.

19. A system as claimed in claim 1 or claim 10 in which the electrodes are wound around the elongated element in helical fashion such that the pitch of the coil is substantially larger than the major cross-sectional dimension of the elongated element.

20. An electrochemical system for detection of a fluid component, comprising:
- at least two electrodes;
- an elongated element adapted to hold an electrolyte which combines with the fluid component to be detected to cause a change in an electrical parameter detectable by means of the electrodes, and disposed so that the electrodes are in contact with the electrolyte, the electrolyte being distributed along the length of the elongated element, which extends at least partly around a periphery of a zone containing a source from which said fluid component may be emitted or discharged, said elongated element comprising strands or fibres woven together to form a cord, cable or string-shaped structure;
- means for maintaining electrolyte distributed over said elongated element; and
- means for routing said element over at least part of the periphery of said zone such that the element is exposed to fluid flow directed outwardly from said zone and laterally towards the element at different points along its length;
- in which at least one of the electrodes is interwoven with the strands or fibres so that the electrodes contact the electrolyte distributed along the elongated element.

21. A system as claimed in claim 20 in which said routing and supporting means routes the elongated element along a generally linear or curvilinear path.

22. An electrochemical system for detection of a fluid component, comprising:
- an electrolyte which combines with the fluid component to be detected to cause a change in an electrical parameter;
- at least two electrodes, in contact with the electrolyte, so that said electrical parameter is detectable thereby;
- an elongated element with said electrolyte distributed along the length thereof, said elongated element having a length at least 50 times greater than its major cross-sectional dimension and extending at least partly around the periphery of a zone containing a source from which said fluid component may be discharged;
- means for maintaining said electrolyte distributed over said element; and
- means for routing and supporting said element over at least part of a periphery of said zone such that the element is exposed to fluid flow directed outwardly from said zone and laterally towards the element at different points along its length, the routing and supporting means comprising an elongate housing forming a generally horizontally extending channel along the base of which the elongated element extends, the elongated element being in contact at least at one point along its length with said electrolyte, said housing being provided with at least one opening extending lengthwise of the housing such that fluid may enter the housing at said at least one opening, and said elongated element and the housing extending in a loop encircling said zone.

23. A system as claimed in claim 22 in which the electrodes are wound around the elongated element in helical fashion such that the pitch of the coil is substantially larger than the major cross-sectional dimension of the elongated element.

24. A system as claimed in claim 22 in which the channel is interrupted at intervals along its length by reservoirs of electrolyte into which the elongate element dips to provide capillary feed of electrolyte from said reservoirs to the remainder of said elongated element.

25. A system as claimed in claim 22 in which the elongated element comprises strands or fibres woven together to form a cord, cable or string-shaped structure.

* * * * *